United States Patent [19]
Haber et al.

[11] Patent Number: 5,619,752
[45] Date of Patent: Apr. 15, 1997

[54] PUNCTURE EVIDENT SURGICAL GLOVE

[75] Inventors: Terry M. Haber, El Toro; William H. Smedley, Lake Elsinore; Clark B. Foster, Laguna Niguel, all of Calif.

[73] Assignee: Habley Medical Technology Corporation, Lake Forrest, Calif.

[21] Appl. No.: 628,895

[22] Filed: Apr. 9, 1996

[51] Int. Cl.$^6$ ............................................. A41D 13/10
[52] U.S. Cl. .................................. 2/161.7; 2/168
[58] Field of Search ............................ 2/161.7, 16, 21, 2/167, 168, 159, 161.1, 161.6, 162, 160, DIG. 3; 206/807, 524.8

[56] References Cited

U.S. PATENT DOCUMENTS

| | | | |
|---|---|---|---|
| 3,633,216 | 1/1972 | Schonholtz | 2/168 |
| 3,992,723 | 11/1976 | Lazanas | 2/161.7 |
| 4,295,566 | 10/1981 | Vincek | 206/457 |
| 4,843,014 | 6/1989 | Cukier | 2/168 |
| 4,847,918 | 7/1989 | Sturm | 2/167 |
| 4,901,372 | 2/1990 | Pierce | 2/161.7 |
| 4,961,734 | 10/1990 | Kassman | 604/349 |
| 5,317,760 | 6/1994 | Best | 2/161.7 |
| 5,369,807 | 12/1994 | Cho et al. | 2/161.7 |
| 5,524,294 | 6/1996 | Richardson et al. | 2/161.7 |
| 5,526,536 | 6/1996 | Cartmill | 2/161.7 |

Primary Examiner—Amy B. Vanatta
Attorney, Agent, or Firm—Morland C. Fischer

[57] ABSTRACT

A puncture evident surgical glove having an integral indicator by which to visually and instantaneously alert the wearer of the need to re-glove should the structural integrity of the glove be compromised by a tear or puncture that could expose the wearer to a contagious and potentially life-threatening disease. Outer and inner membranes are spaced from one another around the finger area of the glove to define a hermetically sealed air inlet path. The indicator is a flexible, hemispherically shaped fluid reservoir (e.g. bulb) that is sandwiched between the outer and inner membranes and adapted to have either a relaxed, inflated condition at which the indicator bulb is filled with air or a compressed, evacuated condition at which air is expulsed from the indicator bulb to the atmosphere. The indicator bulb in the aforementioned compressed, evacuated condition is representative of the fact that the structural integrity of the surgical glove is intact and devoid of a compromising puncture wound or tear. However, should the finger area of the glove be punctured or torn whereby the air inlet path between the outer and inner membranes communicates with the atmosphere, the indicator bulb will automatically recover from the compressed, evacuated condition to the relaxed, inflated condition so as to warn the wearer of the need to remove and discard his glove.

11 Claims, 3 Drawing Sheets

PUNCTURE EVIDENT SURGICAL GLOVE

BACKGROUND OF THE INVENTION

1. Field of the Invention

This invention relates to a puncture evident surgical glove having integral indicating means by which to visually and instantaneously alert the wearer should the structural integrity of the glove be compromised by a tear or puncture that could expose the wearer to a contagious and potentially life-threatening disease.

2. Background Art

A rapidly growing problem facing surgeons and health care workers who treat high risk patients is contracting nosocomial infection of hepatitis, AIDS and other contagious diseases through punctured, torn or otherwise structurally compromised surgical gloves. In many instances where a sharp instrument such as a hypodermic needle cannula, scalpel, scissors, and the like, is used in an operating theater, the surgeon will accidentally puncture his glove. This penetration and the unsafe condition resulting therefrom often goes undetected until the surgeon removes his glove at the end of the operation and discovers a collection of blood inside the glove. Should the patient being treated have a contagious disease, the surgeon will be exposed to the possibility of contracting the disease and to the potentially life-threatening effects thereof.

At present, nothing is known by which to accurately, instantaneously and visually alert the health care worker of the need to re-glove as a consequence of a compromise in the structural integrity of his glove caused by a puncture or tear. Therefore, what is needed to combat this potentially life-threatening situation among health care workers is a low cost, easy to manufacture and non-obtrusive indicator to warn health care workers of the unsafe condition described above.

SUMMARY OF THE INVENTION

In general terms, a low cost and easy to manufacture, puncture evident surgical glove is disclosed having an integral, non-obtrusive indicator by which to visually and instantaneously alert a health care worker of the need to re-glove should the structural integrity of the glove be compromised as a consequence of a tear or puncture that could expose the wearer to a contagious and potentially life threatening disease. The glove includes outer and inner elastomeric membranes that are maintained in spaced alignment with one another by means of an air permeable material (e.g. expanded polyethylene or polypropylene) that fills the space therebetween. The space between the outer and inner membranes defines an air flow path that is hermetically sealed from the atmosphere and extends around the finger area of the glove. Sandwiched between the outer and inner membranes is a flexible indicator bulb having a hollow body. Disposed between the hollow body of the indicator bulb and the air flow path between the outer and inner membranes is an air inlet check valve. Disposed between the hollow body of the indicator bulb and an exhaust tube to the atmosphere is an air outlet check valve.

In operation, the hollow body of the indicator bulb and the air flow path between the outer and inner membranes are initially filled with air such that the indicator bulb is inflated in a relaxed condition. The indicator bulb is activated or initialized by applying a pushing force thereagainst so that the bulb is pumped and compressed. The increased pressure in the hollow body of the indicator bulb during pumping causes the inlet and exhaust check valves to open, whereby air trapped within the bulb and the air flow path around the finger area of the glove is expulsed to the atmosphere via the exhaust tube. A vacuum is therefore established in each of the indicator bulb and the air flow path such that the bulb is evacuated and flattened and the outer and inner membranes are squeezed together with the air permeable material compressed therebetween.

Should the finger area of the glove be punctured or torn, air suctioned from the atmosphere will fill the air path between the outer and inner membranes and thereby create a pressure differential relative to the vacuum within the body of the indicator bulb. Accordingly, the air inlet check valve will open and the indicator bulb will automatically expand so as to recover from the flattened, evacuated condition to the inflated, at-rest condition. Upon visually inspecting the now inflated indicator bulb, the health care worker will be instantaneously alerted to the potentially unsafe condition and the need to re-glove.

DETAILED DESCRIPTION

Figure 1:
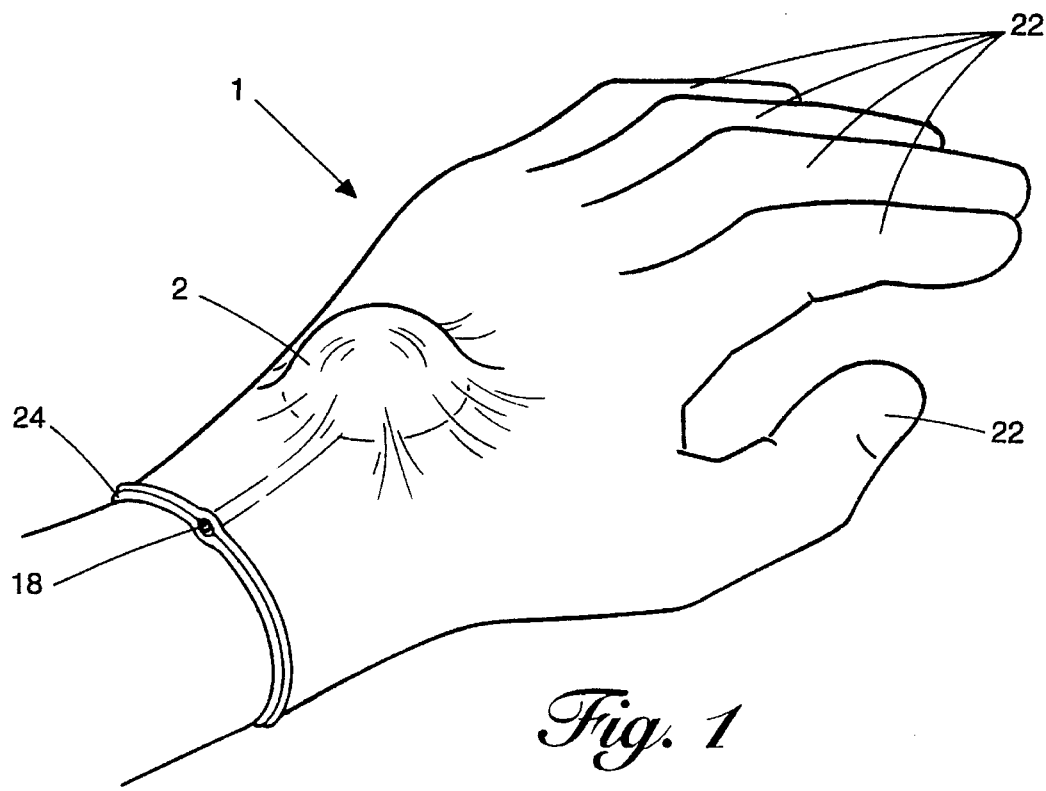
FIG. 1 shows the puncture evident surgical glove which forms the present invention having an integral indicator bulb in an inflated, at-rest condition.
Figure 2:
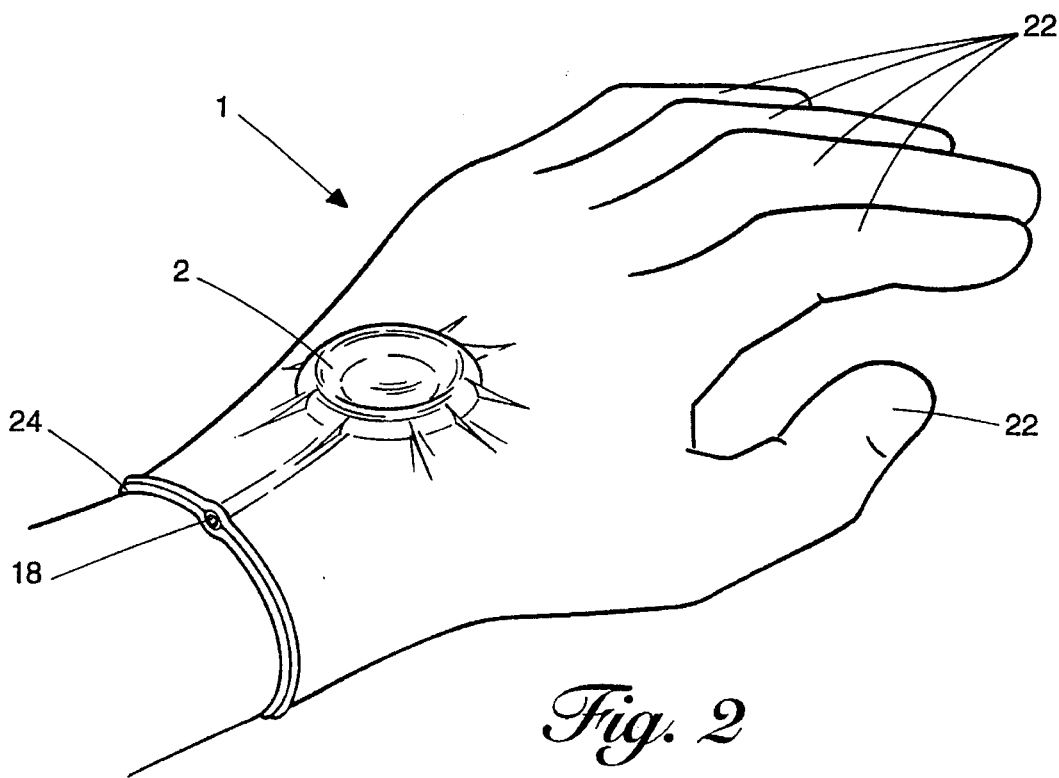
FIG. 2 shows the puncture evident surgical glove of FIG. 1 with the indicator bulb in a compressed, evacuated condition.

The puncture evident surgical glove which forms the present invention is best described while referring to the drawings, where FIGS. 1 and 2 show a glove 1 of the type that would typically be worn by a surgeon or other health care worker who could be exposed to blood and other bodily fluids while operating on or treating a patient. As in conventional surgical gloves, the glove 1 shown in FIGS. 1 and 2 is manufactured from an elastomeric (e.g. latex) material and includes the usual finger area 22 at one end and a pressure cuff 24 at the opposite end. In the case of FIG. 1, and in accordance with the present improvement, the surgical glove is shown with a flexible, hemispherically shaped fluid reservoir (e.g. an indicator bulb 2) in a relaxed (i.e. inflated) condition which is representative of the glove 1 both before the indicator bulb 2 has been activated in a manner to be described hereinafter and after the bulb 2 has been activated and the glove has been compromised by a puncture or tear from a needle cannula or sharp instrument that could expose the wearer to a contagious and possibly life threatening disease should the patient's blood or bodily fluid enter the glove through the puncture or tear. In the case of FIG. 2, the surgical glove is shown with the indicator bulb 2 in a compressed (i.e. evacuated) condition which is representative of the fact that the structural integrity of the glove is intact and does not have any punctures or tears which might compromise the safety of the wearer.

Figure 3:
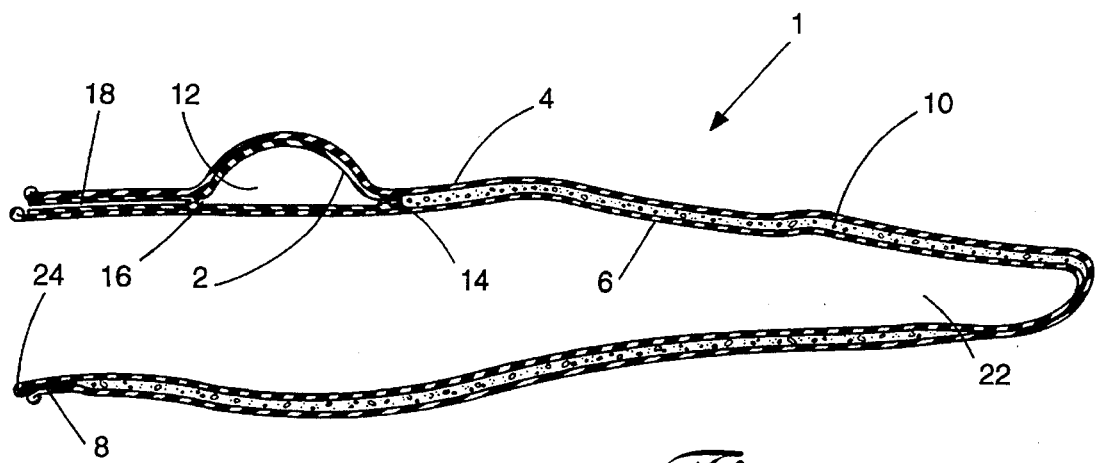
FIG. 3 is a cross-section of the puncture evident surgical glove of FIG. 1 showing the indicator bulb in the inflated, at-rest condition.
Figure 5:
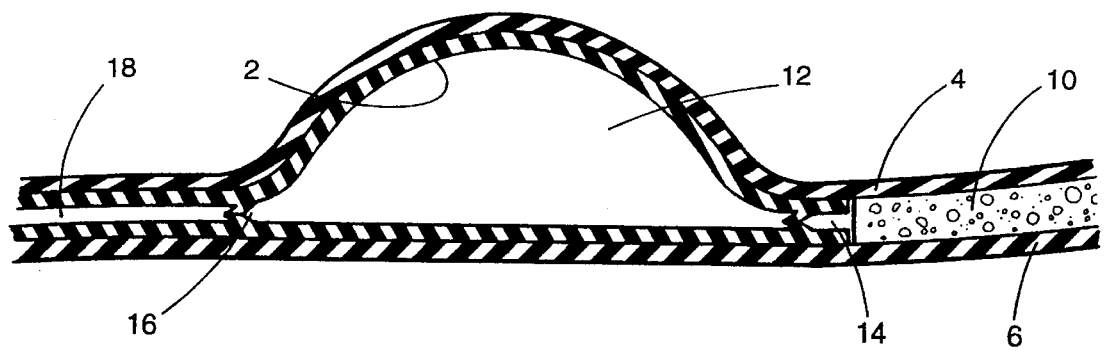
FIG. 5 is an enlarged cross-section showing details of the indicator bulb of FIG. 3 in the inflated, at-rest condition.

FIGS. 3 and 5 of the drawings illustrate details of the puncture evident glove 1 of FIG. 1 when the indicator bulb 2 is in the relaxed, inflated condition. The glove 1 includes an outer membrane 4 and an inner membrane 6 that surrounds the finger area 22 and defines an air path therebetween. The outer and inner membranes 4 and 6 are closed together at a peripheral seal 8 extending completely around the cuff 24 of the glove 1 by means of a rubber adhesive, or the like (best shown in FIG. 3), so that the air path between the outer and inner membranes 4 and 6 is hermetically sealed and isolated from the atmosphere. The air path established between the outer and inner membranes 4 and 6 is filled with an air permeable material 10 (e.g. expanded polyethylene or polypropylene). The air permeable material 10 maintains the air path in the finger area 22 of the glove 1 by preventing the opposing outer and inner membranes 4 and 6 from being pinched together.

The indicator bulb 2 includes a hollow body 12 that is sandwiched between the outer and inner membranes 4 and 6. As is best shown in FIG. 5, the indicator bulb 2 also includes an air inlet and an air exhaust. The air inlet is a one-way check valve 14 that is disposed between the body 12 of bulb 2 and the air path formed between the outer and inner membranes 4 and 6. The air exhaust is also a one-way check valve 16 that is disposed between the body 12 of bulb 2 and an exhaust tube 18 that runs longitudinally along the glove to the cuff 24 (best shown in FIGS. 1 and 2).

Figure 4:
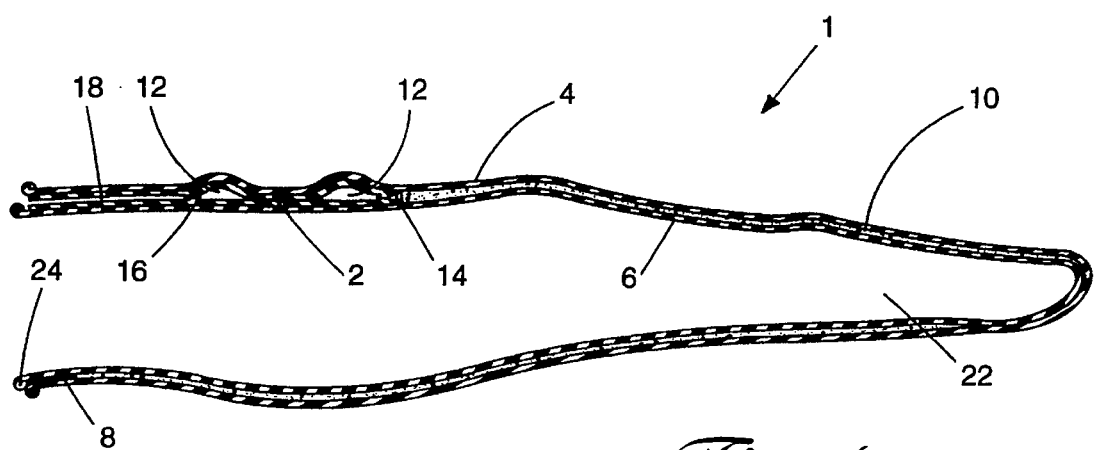
FIG. 4 is a cross-section of the puncture evident surgical glove of FIG. 2 showing the indicator bulb in the compressed, evacuated condition.
Figure 6:
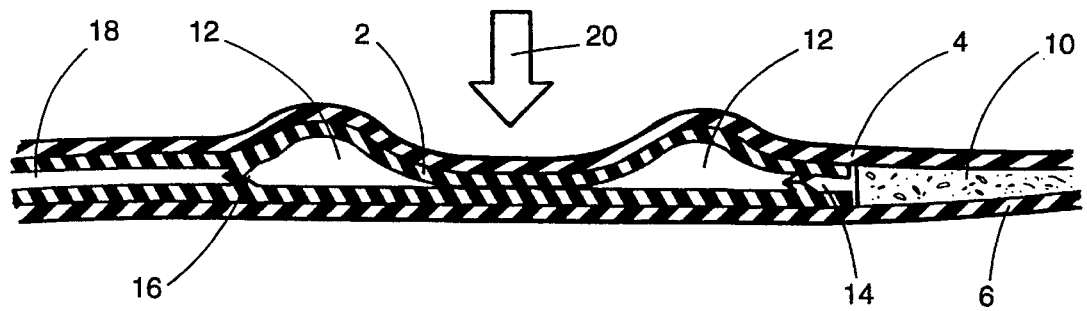
FIG. 6 is an enlarged cross-section showing details of the indicator bulb of FIG. 4 in the compressed, evacuated condition.

Turning now to FIGS. 4 and 6 of the drawings, the operation of the indicator bulb 2 of the puncture evident glove 1 of FIG. 2 is now disclosed for providing an instantaneous, accurate and visual indication to the wearer that the glove has been punctured and the wearer is exposed to the risk of contracting disease. More particularly, with the air inlet and air outlet check valves 14 and 16 closed and the hollow body 12 of the indicator bulb 2 initially relaxed and isolated from the air flow path between the outer and inner membranes 4 and 6 of the glove 1 and from the exhaust tube 18, the wearer exerts a pushing force (in the direction of the reference arrow 20 of FIG. 6) so as to pump the indicator bulb 2.

Accordingly, all of the air that is trapped between the outer and inner membranes 4 and 6 and stored within the hollow body 12 of the indicator bulb 2 is expulsed therefrom to the atmosphere via the exhaust tube 18. That is to say, the increased pressure that is generated within the body 12 of the indicator bulb 2 during the pump strokes will cause the one-way air exhaust check valve 16 to open. In this same regard, the one-way air inlet check valve 14 will open momentarily during the pump strokes, so that all of the air within indicator bulb 2 as well as the air flow path around the finger area 22 of the glove 1 will be evacuated to the atmosphere via exhaust tube 18, whereby the bulb 2 will be compressed (i.e. flattened) and a vacuum condition established in the body 12 thereof. Similarly, a vacuum condition will also be established in the air flow path around the finger area 22 of the glove 1 to cause the outer and inner membranes 4 and 6 to collapse with the air permeable material 10 compressed therebetween.

The indicator bulb 2 will remain in the compressed, evacuated condition of FIGS. 4 and 6 as long as the structural integrity of the surgical glove 1 remains intact and devoid of a puncture wound. However, in the event that the finger area 22 of the glove 1 is punctured or torn (e.g. by a needle cannula, scalpel, scissors, or the like), the indicator bulb will instantaneously respond to provide a visual indication to the wearer of a potentially unsafe condition.

More particularly, a puncture in the finger area 22 of the surgical glove 1 will place the air path located between the outer and inner membranes 4 and 6 in fluid communication with the atmosphere. The resulting pressure differential between the vacuum condition within the indicator bulb 2 and the atmospheric pressure within the air flow path between the outer and inner membranes 4 and 6 will cause the one-way air inlet check valve 14 to open so that air will be suctioned into the body 12 of the indicator bulb 2. Accordingly, and inasmuch as the one-way air exhaust check valve 16 will remain closed as the indicator bulb 2 is filled with air, the indicator bulb 2 will automatically recover from the compressed, evacuated condition of FIGS. 2, 4 and 6 to the relaxed, inflated condition of FIGS. 1, 3 and 5. Similarly, the outer and inner membranes 4 and 6 will separate from one another as air fills the air path therebetween.

Upon visually inspecting the now inflated condition of the indicator bulb 2, the surgeon or other health care worker will be instantaneously advised of a potentially unsafe condition and the need to remove and discard the glove, the structural integrity of which having been compromised by a puncture wound therethrough. The surgeon may then replace the original glove with a new glove and actuate (i.e. pump) the indicator bulb thereof in the manner described above so as to be certain that the new glove is safe and that he will not be exposed to disease that might otherwise have been transmitted through the puncture wound in the structurally compromised glove.

It will be apparent that while a preferred embodiment of the invention has been shown and described, various modifications and changes may be made without departing from the true spirit and scope of the invention. For example, although the flexible indicator bulb 2 of puncture evident surgical glove 1 has been described as being filled with air from the atmosphere to provide a visual warning of a potentially unsafe condition and the need for the wearer to re-glove, it is to be understood that other fluids, such as gases and liquids, may be substituted therefor.

Having thus set forth the preferred embodiment of the present invention, what is claimed is:

1. A puncture evident surgical glove including a finger area in which the wearer's fingers are received, and comprising:

flexible indicator means having a fluid inflated condition at which said indicator means is filled with a fluid from a source of fluid and a fluid evacuated condition at which the fluid is expulsed from said indicator means to said source of fluid;

a fluid exhaust path extending between said flexible indicator means and said source of fluid through which the fluid from said indicator means is expulsed to said source of fluid when said indicator means is compressed to said fluid evacuated condition; and a fluid inlet path extending between said source of fluid and said flexible indicator means through which the fluid from said source of fluid is supplied to fill said indicator means and thereby cause said indicator means to expand to said fluid inflated condition from said fluid evacuated condition, said fluid inlet path extending around the finger area of said surgical glove.

2. The puncture evident surgical glove recited in claim 1, wherein said source of fluid is the atmosphere and the fluid expulsed to and supplied from said source of fluid is air.

3. The puncture evident surgical glove recited in claim 1, wherein said fluid exhaust path includes a one-way check valve that is adapted to open when said flexible indicator means is compressed to said fluid evacuated condition and the fluid is expulsed from said indicator means to said source of fluid.

4. The puncture evident surgical glove recited in claim 3, wherein said fluid exhaust path also includes an exhaust tube connected between said one-way check valve and said source of fluid.

5. The puncture evident surgical glove recited in claim 1, wherein said fluid inlet path includes a one-way check valve that is adapted to open when said flexible indicator means is compressed to said fluid evacuated condition and the fluid is expulsed from said indicator means to said source of fluid and when said flexible indicator means is filled with the fluid from said source of fluid to cause said indicator means to expand to said fluid inflated condition from said fluid evacuated condition.

6. The puncture evident surgical glove recited in claim 1, wherein said fluid inlet path includes an outer membrane and an inner membrane and means by which to separate said outer and inner membranes from one another to establish a space between said outer and inner membranes through which the fluid from said source of fluid is supplied to fill said flexible indicator means to said fluid inflated condition.

7. The puncture evident surgical glove recited in claim 6, wherein said means to separate said outer and inner membranes of said fluid inlet path from one another is a fluid permeable material located between said outer and inner membranes.

8. The puncture evident surgical glove recited in claim 6, wherein said flexible indicator means is sandwiched between said outer and inner membranes of said fluid inlet path.

9. The puncture evident surgical glove recited in claim 6, wherein said flexible indicator means is a hollow fluid reservoir, the compression of said hollow fluid reservoir to said fluid evacuated condition creating a vacuum within said hollow fluid reservoir such that fluid trapped in the space established between said outer and inner membranes of said fluid inlet path is expulsed to said source of fluid via said hollow fluid reservoir and said fluid exhaust path.

10. The puncture evident surgical glove recited in claim 6, wherein the space established between said outer and inner membranes of said fluid inlet path is hermetically sealed and fluidically isolated from said source of fluid.

11. The puncture evident surgical glove recited in claim 10, wherein said flexible indicator means in said fluid evacuated condition is responsive to a hole through the finger area of said glove, whereby the space established between said outer and inner membranes of said fluid inlet path extending around said finger area is unsealed and placed into fluid communication with said source of fluid, such that said indicator means is filled with the fluid from said source of fluid via said space between said outer and inner membranes to automatically expand to said fluid inflated condition from said fluid evacuated condition.

* * * * *